(12) United States Patent
Song (10) Patent No.: US 11,730,957 B2
(45) Date of Patent: Aug. 22, 2023

(54) NERVE STIMULATOR

(71) Applicant: KOREA UNIVERSITY RESEARCH AND BUSINESS FOUNDATION, Seoul (KR)

(72) Inventor: Jae Jun Song, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 79 days.

(21) Appl. No.: 16/955,775

(22) PCT Filed: Dec. 18, 2018

(86) PCT No.: PCT/KR2018/010290
§ 371 (c)(1),
(2) Date: Jul. 10, 2020

(87) PCT Pub. No.: WO2019/142995
PCT Pub. Date: Jul. 25, 2019

(65) Prior Publication Data
US 2020/0346008 A1   Nov. 5, 2020

(30) Foreign Application Priority Data
Jan. 18, 2018  (KR) .................. 10-2018-0006678

(51) Int. Cl.
*A61N 1/36* (2006.01)
*A61N 1/04* (2006.01)
*A61N 1/05* (2006.01)
*H04R 25/00* (2006.01)

(52) U.S. Cl.
CPC ............. *A61N 1/36* (2013.01); *A61N 1/0456* (2013.01); *A61N 1/0492* (2013.01);
(Continued)

(58) Field of Classification Search
CPC ................ A61N 1/0456; A61N 1/0492; A61N 1/36036; A61N 1/3614
See application file for complete search history.

(56) References Cited

U.S. PATENT DOCUMENTS

| 8,265,766 B1 | 9/2012 | Kulkarni et al. |
| 2006/0064139 A1 | 3/2006 | Chung |

(Continued)

FOREIGN PATENT DOCUMENTS

| CN | 103908747 A | 7/2014 |
| KR | 10-2004-000319 A | 1/2004 |

(Continued)

OTHER PUBLICATIONS

International Search Report dated Jan. 17, 2019, issued in PCT Application No. PCT/KR2018/010290, filed Sep. 4, 2018.

(Continued)

*Primary Examiner* — Alyssa M Alter
(74) *Attorney, Agent, or Firm* — Workman Nydegger (57) ABSTRACT

A nerve stimulator according to one embodiment comprises: a pad member including a first pad portion arranged so as to come into contact with the auricle, and a second pad portion arranged so as to come in contact with the external auditory meatus; and a plurality of electrode members provided in the pad member so as to output electro-stimulation, wherein the plurality of electrode members can comprise: a first electrode member provided in the first pad portion so as to come into contact with the auricle; and a second electrode member provided in the second pad portion so as to come into contact with the external auditory meatus.

10 Claims, 6 Drawing Sheets

(52) U.S. Cl.
CPC .......... *A61N 1/0526* (2013.01); *H04R 25/65* (2013.01); *H04R 25/75* (2013.01)

(56) References Cited

U.S. PATENT DOCUMENTS

| | | |
|---|---|---|
| 2007/0150027 A1 | 6/2007 | Rogers |
| 2011/0172744 A1* | 7/2011 | Davis ................... A61N 1/3614 607/62 |
| 2013/0006324 A1 | 1/2013 | Bradley |
| 2013/0103118 A1* | 4/2013 | Magee ................. A61N 1/0456 607/62 |
| 2016/0279021 A1 | 9/2016 | Hyde et al. |
| 2017/0027812 A1* | 2/2017 | Hyde ..................... G16H 10/20 |
| 2017/0113033 A1* | 4/2017 | Wingeier ............. A61B 5/6814 |
| 2017/0333710 A1 | 11/2017 | Shimada |

FOREIGN PATENT DOCUMENTS

| | | |
|---|---|---|
| KR | 10-0799197 B1 | 1/2008 |
| KR | 10-2013-0022274 A | 3/2013 |
| KR | 10-1468355 B1 | 12/2014 |
| WO | WO2017-091705 | 6/2017 |

OTHER PUBLICATIONS

Written Opinion dated Jan. 17, 2019, issued in PCT Application No. PCT/KR2018/010290, filed Sep. 4, 2018.
European Search Report dated Oct. 14, 2021 for KR 18901339.4.

* cited by examiner

NERVE STIMULATOR

TECHNICAL FIELD

The present invention relates to a nerve stimulator, and more particularly, to a nerve stimulator that may output an optimal electrical stimulation for a nerve.

BACKGROUND ART

Tinnitus may have a serious influence on a quality of life of a patient, including sleep, work and psychological problems, depending on the severity thereof. Various therapies for treatment of tinnitus include, for example, a pharmacological therapy, a ganglion block therapy, a surgical therapy, a masking therapy, a magnetic field therapy, or a tinnitus retraining therapy. Among these, the tinnitus retraining therapy is recognized as the most effective therapy for tinnitus treatment.

The tinnitus retraining therapy includes a continuous counseling therapy (directive counseling) that changes negative thoughts about tinnitus, and a sound therapy that uses a sound generator (or a hearing aid) that gradually reduces sensitivity to tinnitus.

The sound therapy is largely divided into two types. When hard of hearing is accompanied, environmental sound is amplified by wearing a hearing aid. When hard of hearing is not accompanied, a sound generator is used.

Sound generators are classified into a hearing aid type, an MP3 type, and a desk type according to shapes thereof. The most effective and proven hearing aid type sound generators are mostly expensive imported goods, and have a difficulty in presenting customized sound. An MP3 type sound generator or a desk type sound generator may relatively selectively present sounds, but have limitations of time/space, and the effect is not proven.

Thus, there is a need to develop a tinnitus treatment device effective for tinnitus treatment at a competitive price.

DISCLOSURE OF INVENTION

Technical Goals

An aspect is to provide a nerve stimulator that may determine an optimal electrical stimulation pattern after measuring a human body impedance using a plurality of electrode members, to allow the plurality of electrode members to effectively output electrical stimulations.

Another aspect is to provide a nerve stimulator that may be manufactured to be customized to a shape of an ear of a user (for example, a patient) through three-dimensional (3D) scanning of the ear.

Another aspect is to provide a nerve stimulator that may deliver an electrical stimulation to a wide portion of an ear region and may allow a plurality of electrode members to selectively output electrical stimulations.

Another aspect is to provide a nerve stimulator that may be capable of simultaneously delivering an electrical stimulation and a sound stimulation, and may increase a plasticity of a cerebral cortex by stimulating an autonomic nervous system of an ear region with the electrical stimulation, to enhance a tinnitus treatment effect by sound sources.

Another aspect is to provide a nerve stimulator that may provide an optimal electrical stimulation to a vagus nerve, to enhance a treatment effect on depression, epilepsy, dementia, and the like.

Technical Solutions

According to an aspect of the present invention, there is provided a nerve stimulator including a pad member including a first pad portion arranged to come into contact with an auricle, and a second pad portion arranged to come into contact with an external auditory meatus; and a plurality of electrode members provided in the pad member and configured to output electrical stimulations, wherein the plurality of electrode members include a first electrode member provided in the first pad portion to come into contact with the auricle; and a second electrode member provided in the second pad portion to come into contact with the external auditory meatus.

According to an aspect, the first pad portion may be formed to be bent to come into contact with the auricle, and the second pad portion may be formed to protrude from a surface of the first pad portion toward the external auditory meatus.

According to an aspect, the plurality of electrode members may be evenly distributed on the pad member, and the second electrode member may be longer than the first electrode member.

According to an aspect, the pad member may be formed of an insulating rubber or a silicone material, the plurality of electrode members may be formed of an electrically conductive rubber or a silicone material, and the pad member and the plurality of electrode members may be manufactured to be customized to a shape of a user's ear.

According to an aspect, the nerve stimulator may further include a control member disposed under the pad member and configured to control electrical stimulations by the plurality of electrode members, and electrical stimulations may be selectively output from the plurality of electrode members by the control member.

According to an aspect, the plurality of electrode members may extend downward through the pad member and may be electrically connected to the control member.

According to an aspect, the nerve stimulator may further include a substrate member disposed under the control member and electrically connected to the plurality of electrode members; and a case member connected to a lower end of the pad member and configured to accommodate the control member and the substrate member therein.

According to an aspect, the nerve stimulator may further include a sound output member configured to output a sound stimulation to a nerve. The sound output member may be mounted on the substrate member and penetrate the control member and the second pad portion.

According to another aspect of the present invention, there is provided a nerve stimulator including a pad member provided to come into contact with a body; a plurality of electrode members provided in the pad member and configured to output electrical stimulations to the body; and a control member configured to control electrical stimulations by the plurality of electrode members, wherein the control member is configured to control the plurality of electrode members to sequentially or simultaneously output electrical stimulations, and configured to detect a human body impedance by the electrical stimulations output from the plurality of electrode members.

According to an aspect, the control member may be configured to determine an optimal electrical stimulation pattern based on the human body impedance detected in the plurality of electrode members, and the optimal electrical stimulation pattern may be formed by an electrode member in which a relatively low human body impedance is detected among the plurality of electrode members.

According to an aspect, the control member may be configured to control the plurality of electrode members to selectively output an electrical stimulation based on the determined optimal electrical stimulation pattern.

Effects

By a nerve stimulator according to an example embodiment, an optimal electrical stimulation pattern may be determined after a human body impedance is measured using a plurality of electrode members, to allow the plurality of electrode members to effectively output electrical stimulations.

According to an example embodiment, a nerve stimulator may be manufactured to be customized to a shape of an ear of a user (for example, a patient) through 3D scanning of the ear.

By a nerve stimulator according to an example embodiment, an electrical stimulation may be delivered to a wide portion of an ear region, and electrical stimulations may be allowed to be selectively output from a plurality of electrode members.

By a nerve stimulator according to an example embodiment, an electrical stimulation and a sound stimulation may be simultaneously delivered, and a plasticity of a cerebral cortex may be increased by stimulating an autonomic nervous system of an ear region with the electrical stimulation, to enhance a tinnitus treatment effect by sound sources.

By a nerve stimulator according to an example embodiment, an optimal electrical stimulation may be provided to a vagus nerve, and thus it is possible to enhance a treatment effect on depression, epilepsy, dementia, and the like.

BEST MODE FOR CARRYING OUT THE INVENTION

Hereinafter, example embodiments will be described with reference to the accompanying drawings. In the following description, the same elements will be designated by the same reference numerals although they are shown in different drawings. Further, in the following description of the example embodiments, a detailed description of known functions and configurations incorporated herein will be omitted when it may make the subject matter of the example embodiments rather unclear.

Also, the terms "first," "second," "A," "B," "(a)," "(b)," and the like may be used herein to describe components according to example embodiments. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

A component having a common function with a component included in one example embodiment is described using a like name in another example embodiment. Unless otherwise described, description made in one example embodiment may be applicable to another example embodiment and detailed description within a duplicate range is omitted.

Figure 1:
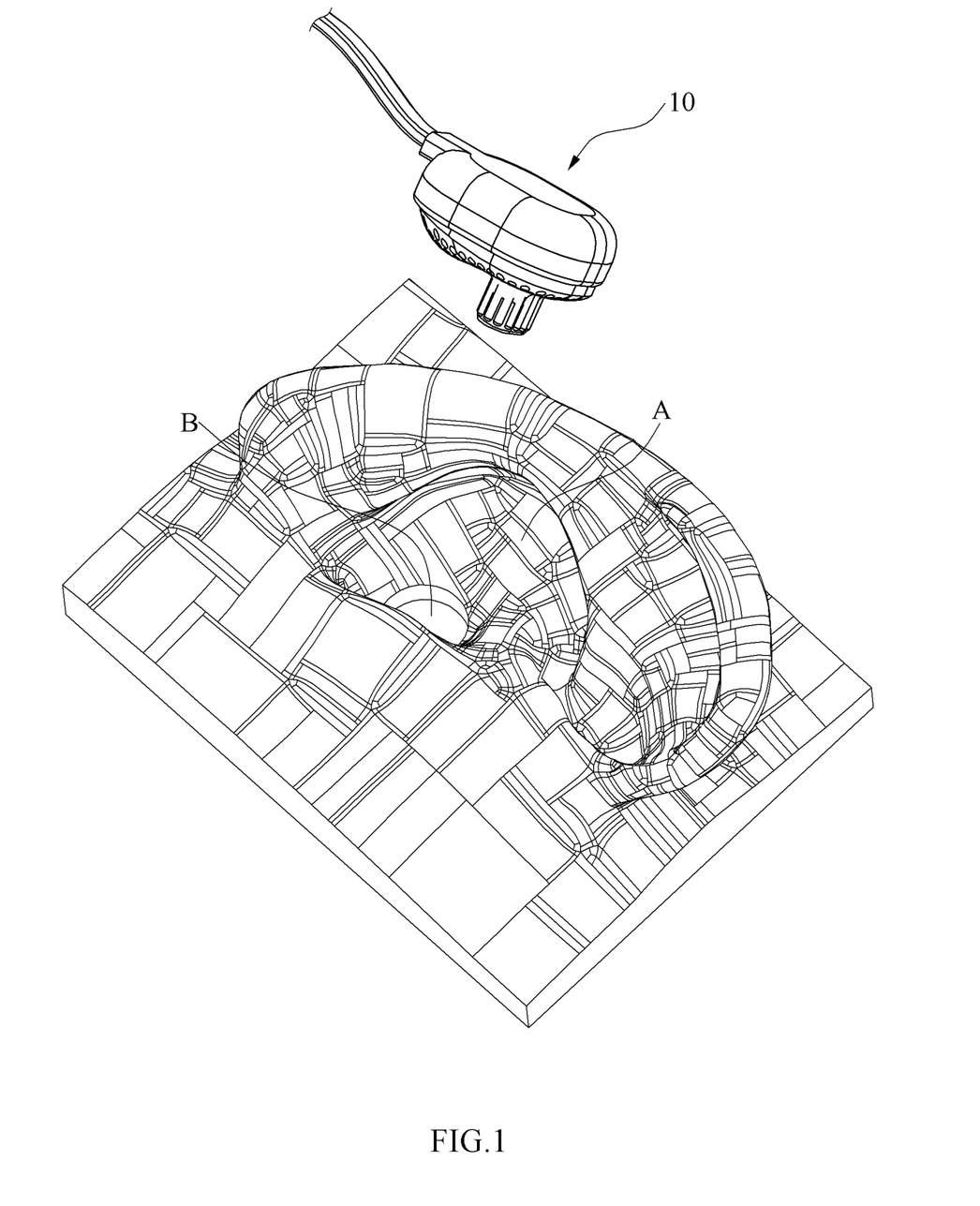
FIG. 1 illustrates a nerve stimulator according to an example embodiment.
Figure 2:
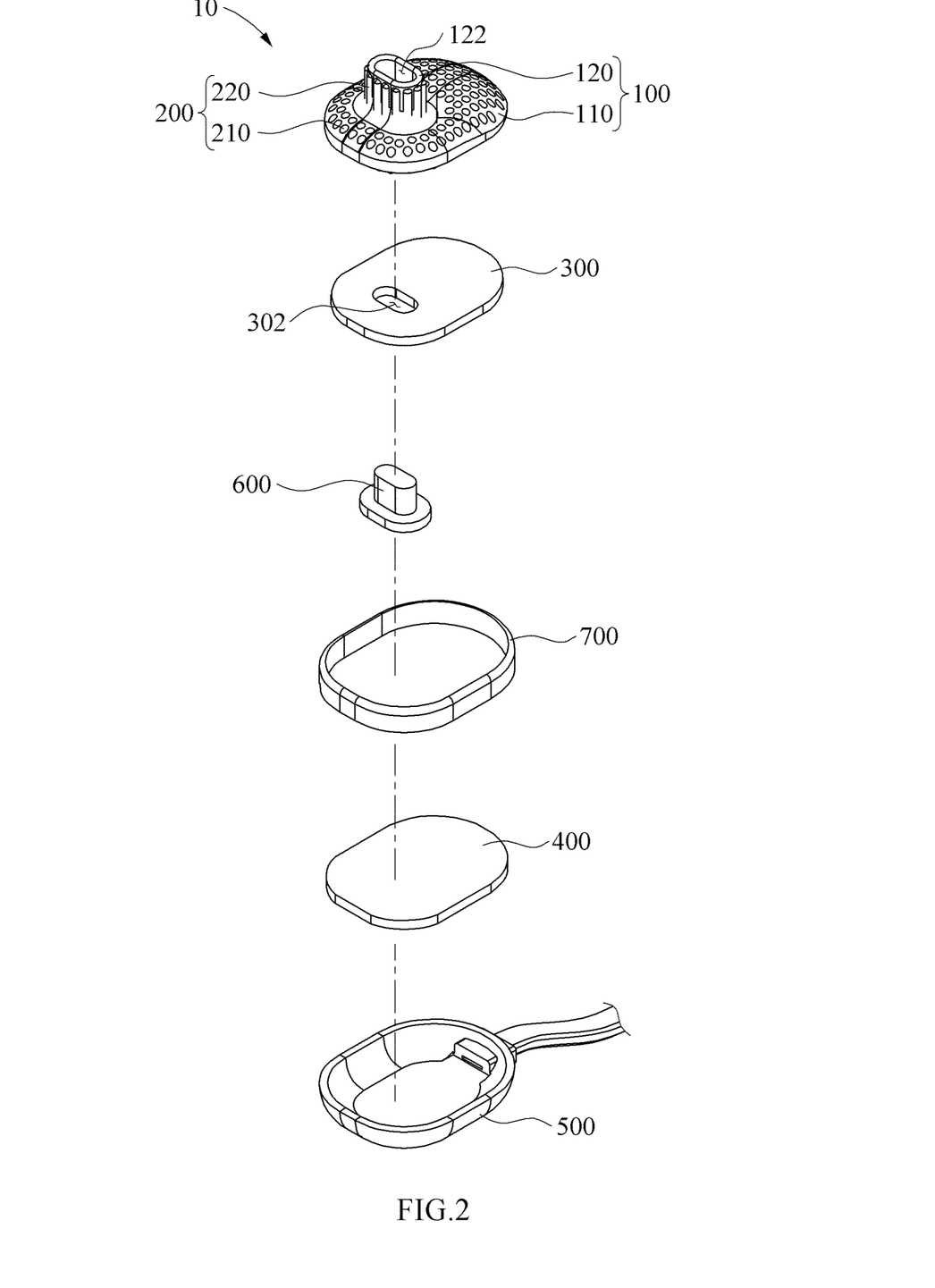
FIG. 2 is an exploded perspective view illustrating a nerve stimulator according to an example embodiment.
Figure 3A:
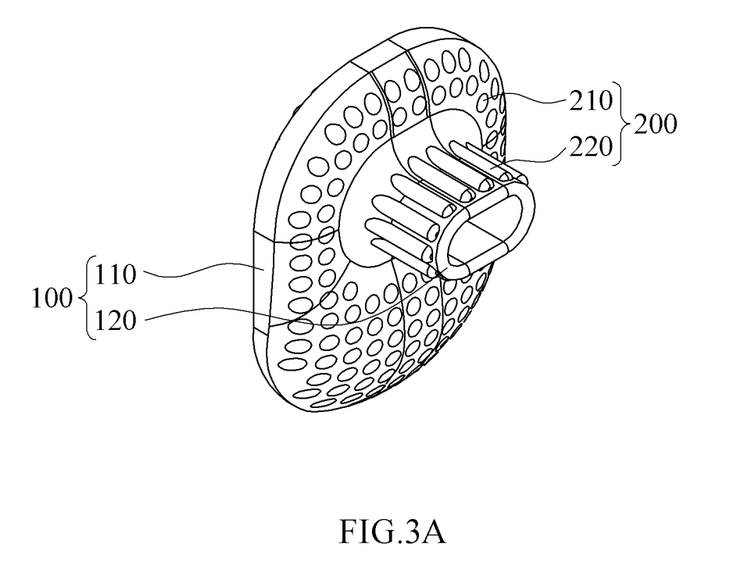
FIGS. 3A and 3B illustrate a pad member and a plurality of electrode members.
Figure 3B:
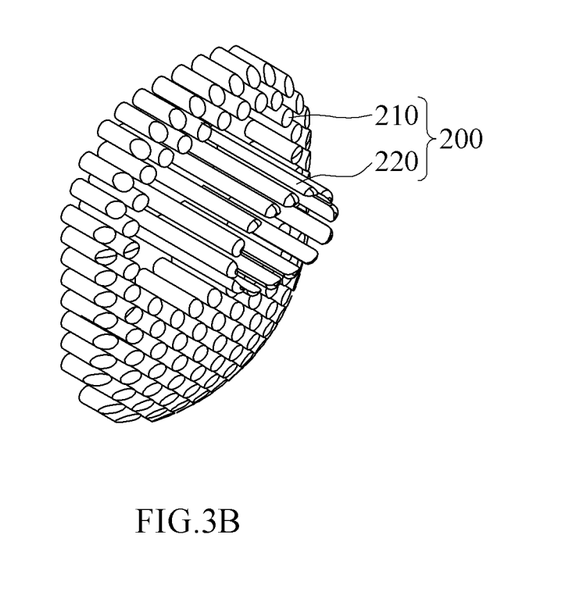
Figure 4:
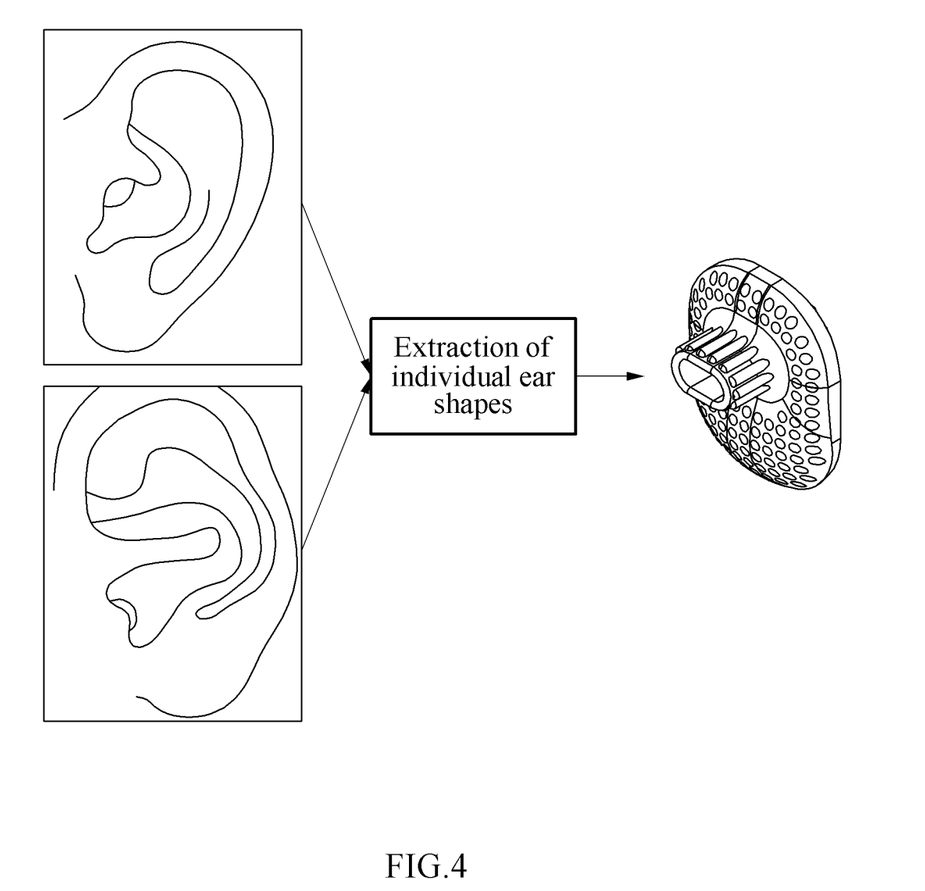
FIG. 4 illustrates an example in which a pad member and a plurality of electrode members are manufactured to be customized to individual's ears.
Figure 5:
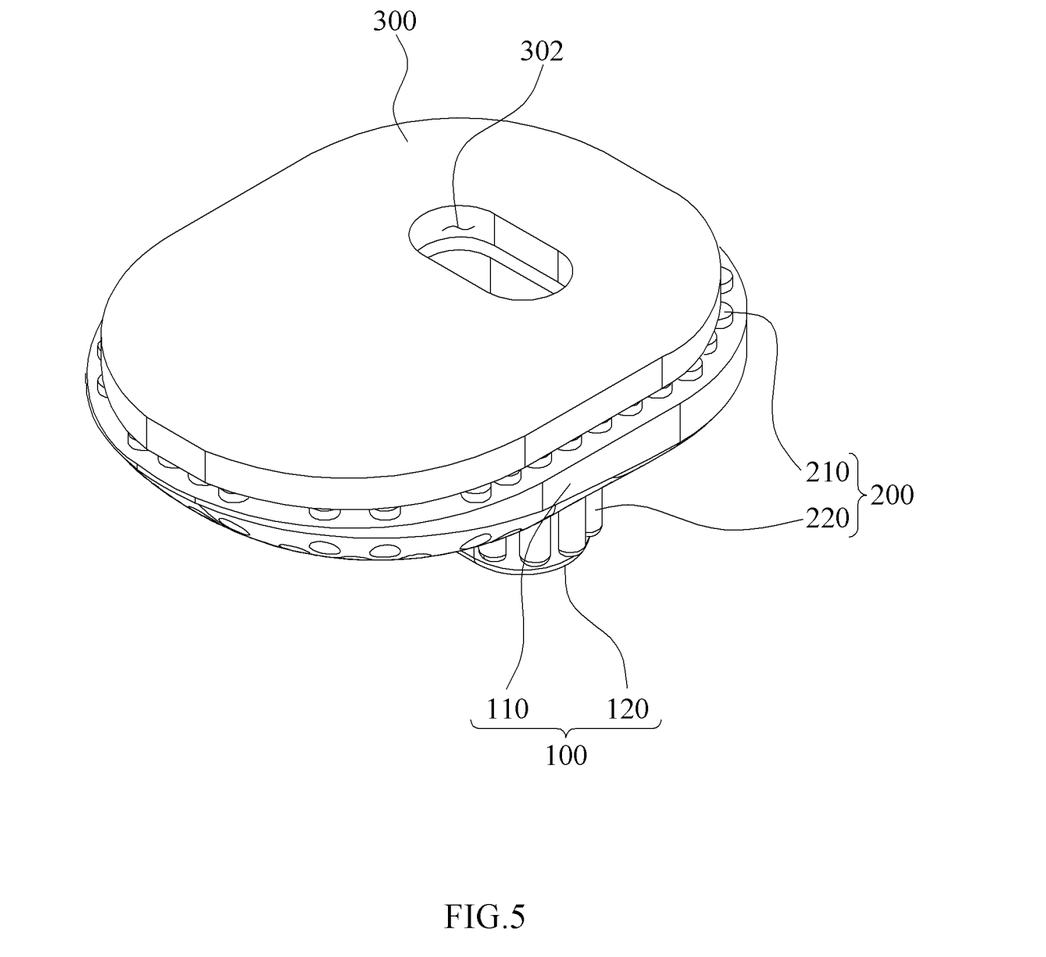
FIG. 5 illustrates an arrangement of a control member.
Figure 6:
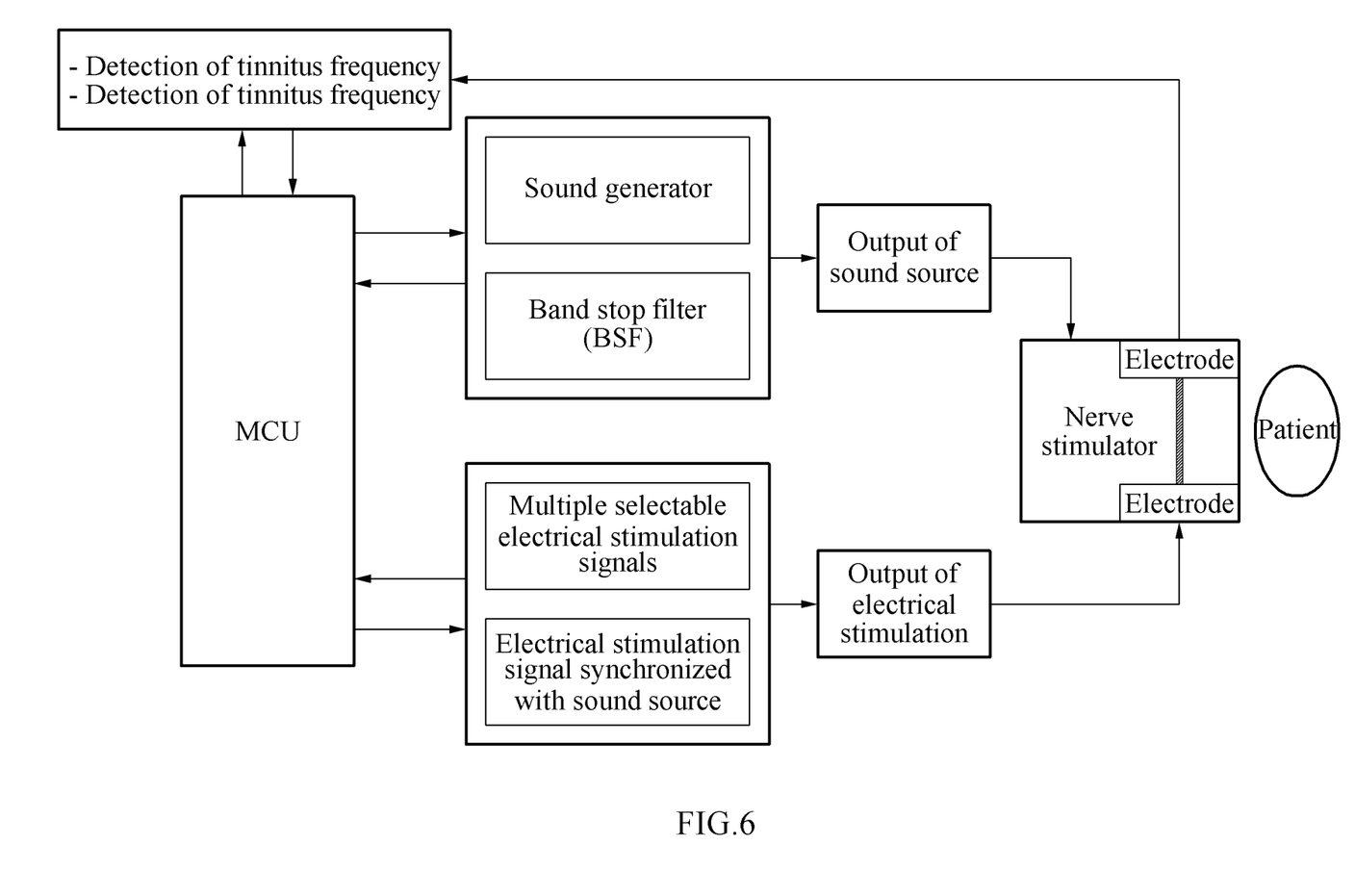
FIG. 6 illustrates a tinnitus treatment process using a nerve stimulator according to an example embodiment.

FIG. 1 illustrates a nerve stimulator according to an example embodiment, and FIG. 2 is an exploded perspective view illustrating a nerve stimulator according to an example embodiment. FIGS. 3A and 3B illustrate a pad member and a plurality of electrode members, and FIG. 4 illustrates an example in which a pad member and a plurality of electrode members are manufactured to be customized to individual's ears. FIG. 5 illustrates an arrangement of a control member, and FIG. 6 illustrates a tinnitus treatment process using a nerve stimulator according to an example embodiment.

Referring to FIGS. 1 and 2, a nerve stimulator 10 according to an example embodiment may include a pad member 100, a plurality of electrode members 200, a control member 300, a substrate member 400, a case member 500, and a sound output member 600.

The pad member 100 may be provided to come into contact with a body to which a nerve stimulation is to be provided.

Hereinafter, an example in which the pad member 100 is in contact with an inner part of an ear to stimulate a vagus nerve in the ear will be described.

For example, the pad member 100 may be mounted inside an ear.

Here, the pad member 100 may have a shape of an earphone, but the shape of the pad member 100 is not limited thereto. The pad member 100 may have any shape capable of being stably mounted inside the ear.

For example, the pad member 100 may be formed of an insulating rubber or a silicone material.

Also, the pad member 100 may include a first pad portion 110 provided to come into contact with an auricle A, and a second pad portion 120 provided to come into contact with an external auditory meatus B.

Here, the first pad portion 110 may be formed to be bent to come into contact with the auricle A, and the second pad portion 120 may be formed to protrude from a surface of the first pad portion 110 toward the external auditory meatus B.

Also, the pad member 100 may include a through hole through which the sound output member 600 penetrates. Specifically, a through hole (not shown) may be formed in the first pad portion 110, and a through hole 122 may also be formed in the second pad portion 120.

The plurality of electrode members 200 may be provided in the above-described pad member 100.

The plurality of electrode members 200 may be formed of an electrically conductive rubber or a silicone material, so as to output electrical stimulations.

For example, the plurality of electrode members 200 may sequentially or simultaneously output electrical stimulations. Outputting of the electrical stimulations from the plurality of electrode members 200 may be individually controlled.

In particular, referring to FIGS. 3A and 3B, the plurality of electrode members 200 may include a first electrode member 210 and a second electrode member 220.

The first electrode member 210 may be provided in the first pad portion 110 to come into contact with an auricle, and the second electrode member 220 may be provided in the second pad portion 120 to come into contact with an external auditory meatus.

Here, the plurality of electrode members 200 may be evenly distributed on the pad member 100.

Specifically, first electrode members 210 may be evenly distributed on a surface of the first pad portion 110, and second electrode members 220 may be evenly distributed around the second pad portion 120. Thus, electrical stimulations may be delivered from the plurality of electrode members 200 in a wider range.

Also, the first electrode member 210 may extend downward through the pad member 100, in particular, the first pad portion 110. A top surface of the first electrode member 210 may be flush with the first pad portion 110, and a bottom surface of the first electrode member 210 may be electrically connected to a top surface of the control member 300. Here, the surface of the first pad portion 110 may be formed to be bent to correspond to a shape of the auricle, and accordingly first electrode members 210 may have different lengths.

The second electrode member 220 may extend downward through the pad member 100, in particular, an area around the second pad portion 120. A top surface of the second electrode member 220 may be flush with an end portion of the second pad portion 120, and the second electrode member 220 may be electrically connected to the top surface of the control member 300. Thus, a length of the second electrode member 220 may be greater than the length of the first electrode member 210.

Referring to FIG. 4, the above-described pad member 100 and plurality of electrode members 200 may be manufactured to be customized to a shape of a user's ear after 3D scanning of the ear. Accordingly, the pad member 100 and the plurality of electrode members 200 may be provided to correspond to a shape of inside of the ear, and thus it is possible to enhance wearing comfort of the pad member 100 and effectively deliver electrical stimulations of the plurality of electrode members 200.

In particular, referring to FIG. 5, the control member 300 may be disposed under the pad member 100.

The control member 300 may be electrically connected to the plurality of electrode members 200, to control electrical stimulations by the plurality of electrode members 200.

Specifically, the control member 300 may control the plurality of electrode members 200 to output electrical stimulations sequentially or simultaneously, and may detect a human body impedance by the electrical stimulations output from the plurality of electrode members 200.

Here, the human body impedance detected by the control member 300 may vary depending on a state of a skin surface. For example, when there is no resistance element at a point of an electrical stimulation by the plurality of electrode members 200, a relatively low human body impedance may be detected by the control member 300. When there is a resistance element at a point of an electrical stimulation by the plurality of electrode members 200, a relatively high human body impedance may be detected by the control member 300. Thus, it may be found that delivering an electrical stimulation to a point at which a relatively low human body impedance is detected by the control member 300 is effective.

Based on the above description, the control member 300 may determine an optimal electrical stimulation pattern based on the detected human body impedance.

Here, the optimal electrical stimulation pattern may be formed by an electrode member 200 in which a relatively low human body impedance is detected among the plurality of electrode members 200.

Finally, the control member 300 may control the plurality of electrode members 200 to selectively output an electrical stimulation based on the optimal electrical stimulation pattern determined as described above.

As described above, the nerve stimulator 10 may allow the plurality of electrode members 200 to output electrical stimulations after the control member 300 determines the optimal electrical stimulation pattern in advance, and may deliver an optimal electrical stimulation to a nerve.

The substrate member 400 may be disposed under the control member 300 and electrically connected to the plurality of electrode members 200. The case member 500 may be connected to a lower end of the pad member 100. Here, the control member 300 and the substrate member 400 may be accommodated in an inner space of the case member 500.

Also, the sound output member 600 may be mounted on the substrate member 400.

The sound output member 600 may output a sound stimulation to a nerve.

Specifically, a lower end of the sound output member 600 may be mounted on a top surface of the substrate member 400, and the sound output member 600 may penetrate the control member 300 and the second pad portion 120 so that a top end of the sound output member 600 and a top end of the second pad portion 120 may be located on the same plane.

For the above arrangement of the sound output member 600, a through hole 302 may be formed in the control member 300, and the through hole 122 may be formed in the second pad portion 120.

In addition, a frame member 700 may be disposed in a position in which the pad member 100 and the case member 500 are coupled. Here, by the frame member 700, the pad member 100 may be fixed with the case member 500, or the pad member 100 may be separated from the case member 500.

Although an example in which the nerve stimulator 10 includes the sound output member 600 have been described above, it is obvious that the sound output member 600 is not included in the nerve stimulator 10, and the nerve stimulator 10 may be configured to deliver only an electrical stimulation to a nerve.

In particular, referring to FIG. 6, the nerve stimulator 10 may be used for tinnitus treatment.

For treatment of a patient with subjective tinnitus who subjectively feels sound in an absence of an external sound stimulation, a sound stimulation by a sound source from which energy of a frequency domain corresponding to a tinnitus frequency is removed, and an electrical stimulation by a plurality of electrode members may be simultaneously delivered, to promote tinnitus treatment.

For example, various tinnitus frequencies and tinnitus magnitudes of a patient may be provided, the patient may be allowed to select sound corresponding to the tinnitus frequency, and tinnitus may be diagnosed. A sound source from which energy of a portion corresponding to the tinnitus frequency of the patient is removed may be produced, and accordingly the sound source may be provided to the patient through the sound output member 600 of the nerve stimulator 10.

In this example, a vagus nerve may be stimulated by outputting electrical stimulations to the auricle and the external auditory meatus using the plurality of electrode members 200 while the sound source is being output, to increase a plasticity of a cerebral cortex. Thus, it is possible to enhance a tinnitus treatment effect by the sound source.

In particular, as described above, the optimal electrical stimulation pattern may be determined by the control member 300, an electrical stimulation may be selectively output from the plurality of electrode members 200, and an output of a sound source and an output of an electrical stimulation may be synchronized, to further enhance the tinnitus treatment effect.

As described above, a nerve stimulator according to example embodiments may determine an optimal electrical stimulation pattern after measuring a human body impedance using a plurality of electrode members, to allow the plurality of electrode members to effectively output electrical stimulations. Also, the nerve stimulator may provide an optimal electrical stimulation to a vagus nerve, to enhance a treatment effect on depression, epilepsy, dementia, and the like, in addition to the tinnitus treatment effect.

While this disclosure includes specific example embodiments, it will be apparent to one of ordinary skill in the art that various changes in form and details may be made in these example embodiments without departing from the spirit and scope of the claims and their equivalents. The example embodiments described herein are to be considered in a descriptive sense only, and not for purposes of limitation. Descriptions of features or aspects in each example embodiment are to be considered as being applicable to similar features or aspects in other example embodiments. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A nerve stimulator comprising:
a pad member provided to come into contact with a body;
a plurality of electrode members provided in the pad member and configured to output electrical stimulations,
wherein the plurality of electrode members comprise:
a first electrode member provided in the first pad portion to come into contact with the auricle; and
a second electrode member provided in the second pad portion to come into contact with the external auditory meatus; and
a sound generator configured for outputting a sound simulation; and
a microcontroller unit (MCU) configured to control electrical stimulations by the plurality of electrode members and the sound simulation, the MCU configured to:
control the plurality of electrode members to output initial electrical stimulations;
detect an impedance at each of the plurality of electrode members;
determine an electrical stimulation pattern comprising at least one low impedance electrode from the plurality of electrode members based on the detected impedance at each of the plurality of electrode members; and
control the at least one low impedance electrode and the sound generator to output the electrical stimulation pattern and the sound simulation.

2. The nerve stimulator of claim 1, wherein the pad member comprises:
a first pad portion arranged to come into contact with an auricle; and
a second pad portion arranged to come into contact with an external auditory meatus.

3. The nerve stimulator of claim 2, wherein:
the first pad portion is formed to be bent to come into contact with the auricle, and
the second pad portion is formed to protrude from a surface of the first pad portion toward the external auditory meatus.

4. The nerve stimulator of claim 1, wherein:
the plurality of electrode members are evenly distributed on the pad member; and
the second electrode member is longer than the first electrode member.

5. The nerve stimulator of claim 1, wherein:
the pad member is formed of an insulating rubber or a silicone material;
the plurality of electrode members are formed of an electrically conductive rubber or a silicone material; and
the pad member and the plurality of electrode members are manufactured to be customized to a shape of a user's ear.

6. The nerve stimulator of claim 1, wherein the control member is disposed under the pad member, and wherein electrical stimulations are selectively output from the plurality of electrode members by the control member.

7. The nerve stimulator of claim 6, wherein the plurality of electrode members extend downward through the pad member and are electrically connected to the control member.

8. The nerve stimulator of claim 6, further comprising:
a substrate member disposed under the control member and electrically connected to the plurality of electrode members; and
a case member connected to a lower end of the pad member and configured to accommodate the control member and the substrate member therein.

9. The nerve stimulator of claim 8, further comprising:
a sound output member configured to output a sound stimulation to a nerve,
wherein the sound output member is mounted on the substrate member and penetrate the control member and the second pad portion.

10. The nerve stimulator of claim 1, wherein the at least one low impedance electrode comprises a plurality of low impedance electrodes but less than a total number of the plurality of electrodes.

\* \* \* \* \*